United States Patent
Sakaguchi et al.

(10) Patent No.: US 6,590,104 B1
(45) Date of Patent: Jul. 8, 2003

(54) PRODUCTION METHOD OF AN ETHER COMPOUND

(75) Inventors: Hiroshi Sakaguchi, Toyonaka (JP); Masaki Sasaki, Misawa (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/349,612

(22) Filed: Jan. 23, 2003

(30) Foreign Application Priority Data

Jan. 25, 2002 (JP) .......................................... 2002-016613

(51) Int. Cl.$^7$ ............................................. C07D 213/64
(52) U.S. Cl. ....................................... 546/301; 546/302
(58) Field of Search .................................. 546/301, 302

(56) References Cited

U.S. PATENT DOCUMENTS

| | | |
|---|---|---|
| 5,872,137 A | 2/1999 | Sakamoto et al. |
| 5,922,880 A | 7/1999 | Sakamoto et al. |

*Primary Examiner*—Patricia L. Morris
(74) *Attorney, Agent, or Firm*—Akin, Gump, Strauss, Hauer & Feld, L.L.P.

(57) ABSTRACT

A production method of an ether compound given by formula (3):

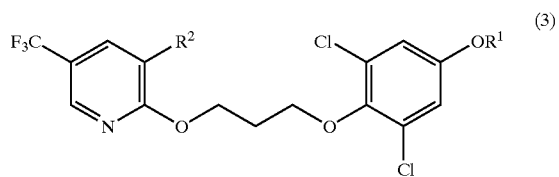

which comprises making an alcohol compound given by formula (4):

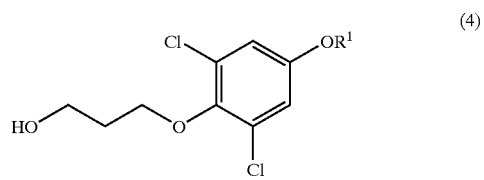

wherein $R^1$ represents a 3,3-dihalo-2-propenyl group or a benzyl group optionally substituted with a halogen atom(s), react with a pyridine compound given by formula (5):

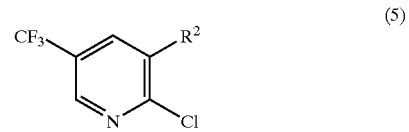

wherein $R^2$ represents a hydrogen atom or halogen atom, in a hydrocarbon compound in the presence of an alkali hydroxide or alkaline earth hydroxide with distilling off water from the reaction mixture, provides the ether compound, which is useful as an active ingredient of insecticide/acaricide or production intermediate thereof, in high yield.

7 Claims, No Drawings

PRODUCTION METHOD OF AN ETHER COMPOUND

TECHNICAL FIELD

The present invention relates to a production method of ether compounds which are useful as active ingredients of insecticide/acaricide or production intermediates thereof.

BACKGROUND ART

It is known that the dihalopropene compounds given by formula (1):

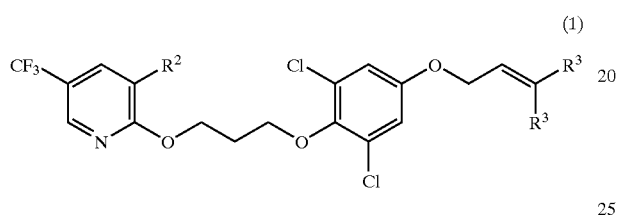

(1)

wherein $R^2$ represents a hydrogen atom or halogen atom and $R^3$ represents a halogen atom, are useful as active ingredients of insecticide/acaricide and that the compounds given by formula (2):

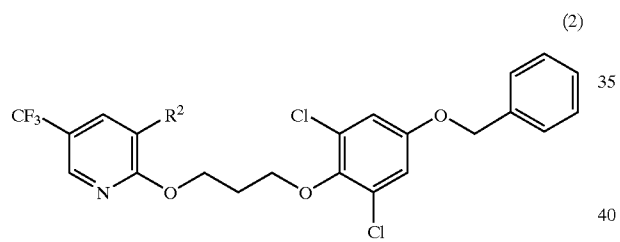

(2)

wherein $R^2$ represents a hydrogen atom or halogen atom, are useful as their production intermediates in U.S. Pat. No. 5,922,880.

The publication also concretely discloses a production method of 1-benzyloxy-3,5-dichloro-4-[3-(5-trifluoromethylpyridin-2-yloxy)propoxy]benzene (the compound given by above formula (2) wherein $R^2$ is a hydrogen atom) by making 3-(2,6-dichloro-4-benzyloxy)phenoxy-1-propyl alcohol react with 2-chloro-5-trifluoromethylpyridine in the presence of a base in N,N-dimethylformamide.

SUMMARY OF THE INVENTION

However, the above method needs N,N-dimethylformamide, which is desired to avoid the use of a large amount in an industrial production, as a solvent and the yield is not satisfactory.

The object of the present invention is to provide a production method of the ether compounds given by formula (3):

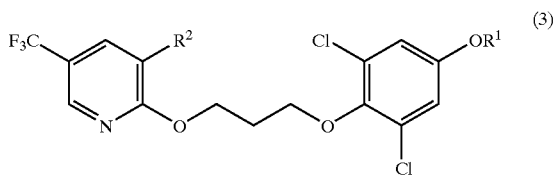

(3)

wherein $R^1$ represents a benzyl group optionally substituted with a halogen atom(s) or 3,3-dihalo-2-propenyl group and $R^2$ represents a hydrogen atom or halogen atom, in high yield by using a hydrocarbon compound that is industrially available as a solvent.

According to the present invention, the ether compound given by formula (3) can be produced by making the alcohol compounds given by formula (4):

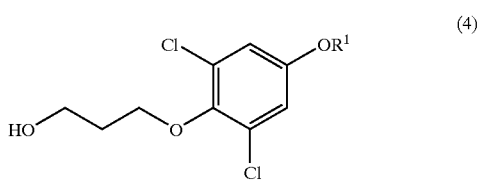

(4)

wherein $R^1$ represents a benzyl group optionally substituted with a halogen atom(s) or 3,3-dihalo-2-propenyl group, react with the pyridine compounds given by formula (5):

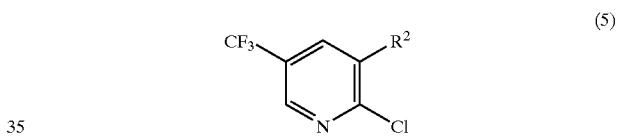

(5)

wherein $R^2$ represents a hydrogen atom or halogen atom, in a hydrocarbon compound in the presence of alkali hydroxide or alkaline earth hydroxide with distilling off water from the reaction mixture in high yield and good quality.

DETAILED DESCRIPTION OF THE INVENTION

In the present invention, the benzyl group optionally substituted with a halogen atom(s) for $R^1$ means a benzyl group or a benzyl group whose hydrogen atom(s) on the benzene ring is/are substituted with at least one halogen atom. Typical examples include benzyl group and 4-chlorobenzyl group. Examples of the 3,3-dihalo-2-propenyl group for $R^1$ include 3,3-dichloro-2-propenyl group and 3,3-dibromo-2-propenyl group.

Examples of the halogen atom for $R^2$ include chlorine atom.

The production method of the present invention is characterized by making the alcohol compound given by formula (4) react with the pyridine compound given by formula (5) in a hydrocarbon compound in the presence of an alkali hydroxide or alkaline earth hydroxide with distilling out water.

The reaction is carried out in a hydrocarbon compound. Examples of the hydrocarbon compound used for the reaction include aliphatic hydrocarbon compounds such as hexane, heptane, octane, nonane, decane, 3-methylpentane, cyclohexane, methylcyclohexane, ethylcyclohexane and so on; and aromatic hydrocarbon compounds such as toluene, xylene, mesitylene, ethylbenzene and so on. The amount of the hydrocarbon compound used for the reaction is usually 0.3 to 50 parts by weight based on 1 part by weight of the alcohol compound given by formula (4), preferably 10 parts by weight or less in the view of the reaction rate.

The ratio of the alcohol compound given by formula (4) to the pyridine compound given by formula (5) used for the reaction is usually 0.9 to 2 mols of the pyridine compound given by formula (5) based to 1 mol of the alcohol compound given by formula (4).

Examples of the alkali hydroxide and alkaline earth hydroxide used for the reaction include lithium hydroxide, sodium hydroxide, potassium hydroxide, calcium hydroxide and barium hydroxide. The amount can be varied so long as the reaction proceeds, and it is usually 0.9 mol or more based on 1 mol of the alcohol compound given by formula (4) and 1.2 mols or less based on 1 mol of the pyridine compound given by formula (5). The alkali hydroxide and alkaline earth hydroxide used for the reaction can be added to the reaction mixture as an aqueous solution.

The reaction temperature is in the range of 50 to 200° C. and the reaction can be carried out under reduced pressure so that water can be easily distilled off from the reaction mixture.

The distillation of water is performed while the reaction is proceeding. The method for distilling off water from the reaction mixture is, for example, 1) performing the reaction at the boiling point of water or more under normal pressure or reduced pressure and distilling off water from the reaction mixture or 2) performing the reaction at the boiling point of the solvent or more under normal pressure or reduced pressure and distilling off water together with the solvent from the reaction mixture.

In the latter case, the solvent can be recycled by using Dean-Stark water-separator and separating the solvent from water in the distillate.

The reaction can be carried out as follows.
1) Mixing the alcohol compound given by formula (4), the pyridine compound given by formula (5), an alkali hydroxide or alkaline earth hydroxide and a hydrocarbon compound, and distilling off water by heating under normal pressure or reduced pressure.
2) Mixing the alcohol compound given by formula (4), the pyridine compound given by formula (5) and a hydrocarbon compound, adding dropwise an aqueous solution of an alkali hydroxide or alkaline earth hydroxide to the mixture while heating under normal pressure or reduced pressure distilling off water, and simultaneously distilling off water.
3) Mixing the pyridine compound given by formula (5), an alkali hydroxide or alkaline earth hydroxide and a hydrocarbon compound, adding dropwise the alcohol compound given by formula (4) to the mixture while heating under normal pressure or reduced pressure, and simultaneously distilling off water.
4) Mixing the pyridine compound given by formula (5) and a hydrocarbon compound, adding dropwise each of an aqueous solution of an alkali hydroxide or alkaline earth hydroxide and the alcohol compound given by formula (4) to the mixture simultaneously while heating under normal pressure or reduced pressure, and simultaneously distilling off water.

The proceeding status of the reaction can be confirmed by analyzing the reaction product with chromatography such as high performance liquid chromatography and the like.

After the reaction, the ether compound given by formula (3) can be isolated by work-up procedures, for example, adding water to the reaction mixture, extracting with an organic solvent and concentrating the obtained organic layer.

The ether compound given by formula (6):

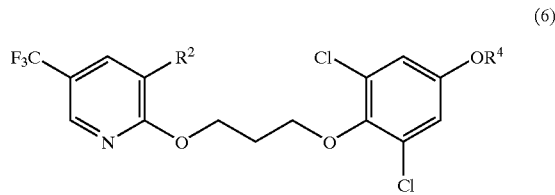

(6)

wherein $R^2$ represents a hydrogen atom or halogen atom and $R^4$ represents a benzyl group optionally substituted with a halogen atom(s), which can be manufactured by the production method of the present invention, can be lead to a dihalopropene compound given by formula (7):

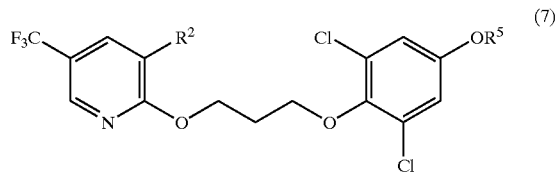

(7)

wherein $R^2$ represents a hydrogen atom or halogen atom and $R^5$ represents a 3,3-dihalo-2-propenyl group, for example, according to the method described in U.S. Pat. No. 5,922,880.

The alcohol compound given by formula (4) can be prepared by the method disclosed in U.S. Pat. No. 5,922,880 or according to the description of U.S. Pat. No. 5,922,880.

EXAMPLES

The present invention is explained in detail below. The present invention is not limited by the following examples.

Example 1

To a mixture of 13.02 g of 2-chloro-5-trifluoromethylpyridine (purity: 96.7%) and 21.14 g of hexane, each of 5.75 g of 48.3% aqueous sodium hydroxide solution and 21.14 g of 3-[2,6-dichloro-4-(3,3-dichloroallyloxy)]phenoxy-1-propyl alcohol (purity: 94.6%) was added simultaneously dropwise over 5 hours under refluxing by heating while distilling off water with Dean-Stark water-separator. After the addition, water was distilled off under refluxing by heating for 20 hours. Then, 32 g of water and 42 g of hexane were added to the reaction mixture and the layers were separated. The organic layer was washed with 32 g of 3% aqueous sodium hydroxide solution, 32 g of 3% hydrochloric acid and 32 g of water subsequently, and concentrated to give 28.62 g of 1-(3,3-dichloroallyloxy)-3,5-dichloro-4-[3-(5-trifluoromethylpyridin-2-yloxy)propyloxy]benzene (purity: 94.6%, yield: 95%).

1-(3,3-Dichloroallyloxy)-3,5-dichloro-4-[3-(5-trifluoromethylpyridin-2-yloxy)propyloxy]benzene

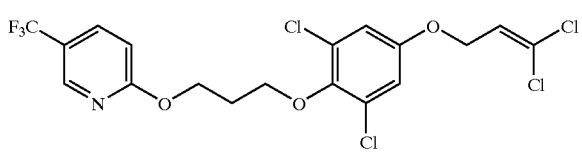

Example 2

To a mixture of 5.00 g of 3-(2,6-dichloro-4-benzyloxy)phenoxy-1-propyl alcohol, 3.15 g of 2-chloro-5-trifluoromethylpyridine and 5.00 g of heptane, 1.43 g of 48.5% aqueous sodium hydroxide solution was added dropwise over 5 hours under refluxing by heating while distilling off water with Dean-Stark water-separator. After the addition, water was distilled off under refluxing by heating for 19 hours. Then, 10 g of water and 10 g of heptane were added to the reaction mixture and the layers were separated. The organic layer was washed with 10 g of 3% aqueous sodium hydroxide solution, 10 g of 5% hydrochloric acid and 10 g of water subsequently, and concentrated to give 6.36 g of 1-benzyloxy-3,5-dichloro-4-[3-(5-trifluoromethylpyridin-2-yloxy)propyloxy]benzene (purity: 96.3%, yield: 90%).

1-Benzyloxy-3,5-dichloro-4-[3-(5-trifluoromethylpyridin-2-yloxy)propyloxy]benzene

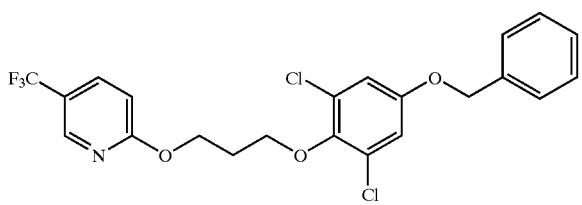

The analysis condition in the examples above is as follows.

In the above-described examples, the purity analysis was performed under the following condition.

High performance liquid chromatography
Column: L-column (manufactured by Chemicals Evaluation and Research Institute, Japan)
Mobile phase: acetonitrile/water=8/2
Flow rate of mobile phase: 1 ml/min.
Column temperature: 40° C.
Detector: UV absorption photometer (Detected wave length: 270 nm)
Internal standard: di(2-ethylhexyl)phthalate

What is claimed is:

1. A production method of an ether compound given by formula (3):

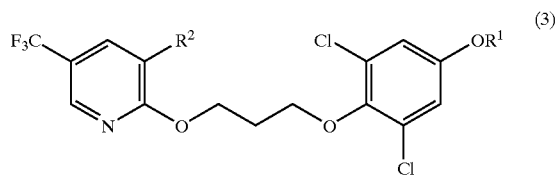

wherein $R^1$ represents a benzyl group optionally substituted with a halo gen atom(s) or 3,3-dihalo-2-propenyl group and $R^2$ represents a hydrogen atom or halogen atom,
which comprises making an alcohol compound given by formula (4):

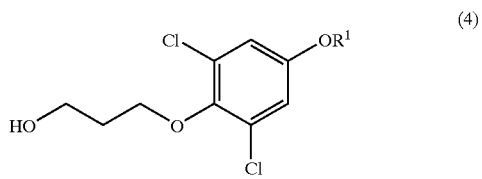

wherein, $R^1$ means as described above,
react with a pyridine compound given by formula (5):

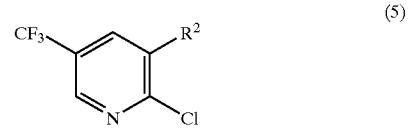

wherein $R^2$ mean as described above,
in a hydrocarbon compound in the presence of an alkali hydroxide or alkaline earth hydroxide with distilling off water from the reaction mixture.

2. A production method of an ether compound according to claim 1, wherein the hydrocarbon compound is an aliphatic hydrocarbon compound.

3. A production method of an ether compound according to claim 1, wherein the hydrocarbon compound is hexane or heptane.

4. A production method of an ether compound according to claim 1, wherein $R^1$ represents a benzyl group optionally substituted with a halogen atom(s).

5. A production method of an ether compound according to claim 1, wherein $R^1$ represents a benzyl group or 4-chlorobenzyl group.

6. A production method of an ether compound according to claim 1, wherein $R^1$ represents a 3,3-dihalo-2-propenyl group.

7. A production method of an ether compound according to claim 1, wherein $R^1$ represents a 3,3-dihalo-2-propenyl group.

* * * * *